US010597682B2

(12) United States Patent
Zhang et al.

(10) Patent No.: US 10,597,682 B2
(45) Date of Patent: Mar. 24, 2020

(54) INOSITOL PREPARATION METHOD (71) Applicant: CHENGDU YUANHONG BIOLOGICAL TECHNOLOGY CO., LTD., Chengdu, Sichuan (CN)

(72) Inventors: Yi-Heng Percival Zhang, Blacksburg, VA (US); Chun You, Tianjin (CN)

(73) Assignee: CHENGDU YUANHONG BIOLOGICAL TECHNOLOGY CO., LTD., Chengdu (CN)

(*) Notice: Subject to any disclaimer, the term of this patent is extended or adjusted under 35 U.S.C. 154(b) by 0 days.

(21) Appl. No.: 15/783,996

(22) Filed: Oct. 13, 2017

(65) Prior Publication Data

US 2018/0057844 A1 Mar. 1, 2018

Related U.S. Application Data (63) Continuation-in-part of application No. PCT/CN2016/076526, filed on Mar. 16, 2016.

(30) Foreign Application Priority Data

Apr. 17, 2015 (CN) .......................... 2015 1 0184621

(51) Int. Cl.
C12P 7/02 (2006.01)
C12N 9/42 (2006.01)

(52) U.S. Cl.
CPC .............. C12P 7/02 (2013.01); C12N 9/2437 (2013.01); C12Y 204/01001 (2013.01); C12Y 204/0102 (2013.01); C12Y 204/01049 (2013.01); C12Y 301/03025 (2013.01); C12Y 504/02002 (2013.01); C12Y 505/01004 (2013.01); C12P 2203/00 (2013.01)

(58) Field of Classification Search
None
See application file for complete search history.

(56) References Cited

U.S. PATENT DOCUMENTS

2004/0063184 A1    4/2004  Grichko
2014/0296497 A1*  10/2014  Konishi ................... C12P 19/46
                                                         536/4.1

FOREIGN PATENT DOCUMENTS

| CN | 1701115 A | 11/2005 |
|---|---|---|
| JP | 2008054506 A | 3/2008 |
| JP | 2010536375 A | 12/2010 |
| JP | 2014064513 A | 4/2014 |
| WO | 2013073483 A1 | 11/2012 |
| WO | 2013096693 A1 | 6/2013 |
| WO | 2013125666 A1 | 8/2013 |
| WO | WO2014/197702 | * 12/2014 |
| WO | 2015001312 A1 | 1/2015 |

OTHER PUBLICATIONS

N.C. Butzin et al. "Reconstructed Ancestral Myo-Inositol-3-Phosphate Synthases Indicate That Ancestors of the *Thermococcales* and *Thermotoga* Species Were More Thermophilic than Their Descendants", PLOS One 8(12): 1-10 (Year: 2013).*

Feng-Jie Yuan et al., "Characterization of D-myo-inositol 3-phosphate Synthase Gene Expression in Two Soybean Low Phytate Mutants", Journal of Nuclear Agricultural Sciences, vol. 27, No. 3, 2013, pp. 286-292.

Chuanbo Dai, "Study on Preparation Method of Inositol from Maceration Water of Corn", Science—Engineering (A), Chinese Selected Doctoral Dissertations and Master's Theses Full-Text Databases (Doctoral, Oct. 15, 2005 (Oct. 15, 2005), pp. 11-12, ISSN: 1671-6779.

Barunava Patra et al: "Functional identification of sll1383 from *Synechocystis* sp PCC 6803 as L-myo-inositol 1-phosphate phosphatase (EC 3.1.3.25): molecular cloning, expression and characterization", Planta ; An International Journal of Plant Biology, Springer, Berlin, DE, vol. 225, No. 6, Nov. 23, 2006 (Nov. 23, 2006), pp. 1547-1558, XP019517467, ISSN: 1432-2048, DOI: 10.1007/S00425-006-0441-7.

T. B. Reynolds: "Strategies for acquiring the phospholipid metabolite inositol in pathogenic bacteria, fungi and protozoa: making it and taking it", Microbiology, vol. 155, No. 5, Apr. 21, 2009 (Apr. 21, 2009), pp. 1386-1396, XP055494367, GB ISSN: 1350-0872, DOI: 10.1099/mic.0.025718-0.

Pham Huynh Ninh et al: "Assembly and multiple gene expression of thermophilic enzymes in *Escherichia coli* for in vitro metabolic engineering", Biotechnology and Bioengineering, vol. 112, No. 1, Jan. 1, 2015 (Jan. 1, 2015), pp. 189-196, XP055476156, US ISSN: 0006-3592, DOI: 10.1002/bit.25338.

Liangjing Chen et al: "Characterization of a Tetrameric Inositol Monophosphatase from the Hyperthermophilic Bacterium Thermotoga maritima", Applied and Environmental Microbiology, Oct. 1, 1999 (Oct. 1, 1999), pp. 4559-4567, XP055494446, United States Retrieved from the Internet: URL:http://aem.asm.org/content/65/10/4559.full.pdf#page=I&view=FitH.

J. A. Brito et al: "Crystal Structure of Archaeoglobus fulgidus CTP: Inositol-1-Phosphate Cytidylyltransferase, a Key Enzyme for Di-myo-Inositol-Phosphate Synthesis in (Hyper)Thermophiles", Journal of Bacteriology, vol. 193, No. 9, May 1, 2011 (May 1, 2011), pp. 2177-2185, XP055494500, US ISSN: 0021-9193, DOI: 10.1128/JB.01543-10.

(Continued)

*Primary Examiner* — Rebecca E Prouty
(74) *Attorney, Agent, or Firm* — Novick, Kim & Lee, PLLC; Allen Xue (57) ABSTRACT An inositol preparation method by enzymatic catalysis uses starch and cellulose or substrates thereof as substrates. Raw materials are converted to inositol by in vitro multi-enzyme reaction system in one pot. The yield from the substrate to inositol is significantly improved by process optimization and adding new enzymes. The new enzymes can promote the phosphorolysis of starch or cellulose and utilization of glucose, which is the final production after the phosphorolysis of starch and cellulose. The inositol preparation method described herein has great potentials in industrial production of inositol because of high inositol yield, easy scale-up, low production cost, and lower impact to environment.

2 Claims, 9 Drawing Sheets (56) References Cited

OTHER PUBLICATIONS

Chun You et al: "An in vitro synthetic biology platform for the industrial biomanufacturing of myo-inositol from starch : Biomanufacturing by in Vitro Synthetic Biology", Biotechnology and Bioengineering, vol. 114, No. 8, Aug. 1, 2017 (Aug. 1, 2017), pp. 1855-1864, XP055494336, US ISSN: 0006-3592, DOI: 10.1002/bit.26314.

Yiping Lu et al: "Production of myo-inositol from glucose by a novel trienzymatic cascade of polyphosphate glucokinase, inositol 1-phosphate synthase and inositol monophosphatase", Enzyme and Microbial. Technology, vol. 112, May 1, 2018 (May 1, 2018), pp. 1-5, XP055494339, US ISSN: 0141-0229, DOI: 10.1016/j.enzmictec.2018.01.006.

European Patent Office, "Supplementary European Search Report" for EP 16779495, dated Jul. 24, 2018.

Japanese Patent Office, Office Action for JP patent application No. 2017-554491, dated Nov. 5, 2018.

Tomoko Fujisawa et al., "An in vitro enzyme system for the production of myo-inositol", Proceedings (online) of the Annual Meeting 2016 Sapporo of Japan Society for Bioscience, Biotechnology, and Agrochemistry, Mar. 5, 2016.

I-Wen Chen et al., "Biochemical Studies on Inositol", the Journal of Biological Chemistry, vol. 239, No. 6, Jun. 1964.

Michael R. Culbertson et al., "Control of Inositol Biosynthesis in *Saccharomyces cerevisiae*: properties of a repressible Enzyme System in Extracts of Wild-Type (Ino+) Cells", Journal of Bacteriology, Apr. 1976, pp. 232-242.

Japanese Patent Office, Office Action for JP patent application No. 2017-554491, dated Jul. 29, 2019.

* cited by examiner

INOSITOL PREPARATION METHOD

The present application is a continuation in part application of International Patent Application No. PCT/CN2016/076526, filed on Mar. 16, 2016, which claims the priority to Chinese Patent Application No. 201510184621.4, titled "Inositol preparation method", filed on Apr. 17, 2015 with the Chinese State Intellectual Property Office, all of which are incorporated herein by reference in their entireties.

FIELD

The present disclosure relates to inositol preparation method, particularly to a method for the conversion of starch or cellulose and their derivative to inositol through multi-enzyme catalysis in vitro, which belongs to the field of enzyme-catalyzed production of inositol.

BACKGROUND

Inositol, also known as cyclohexanehexol, is a member of water-soluble vitamin B family. Inositol is an essential substance for the growth of human, animal and microbial and it is widely used in medicine, food, feed and other industries. The current global demand is about 5,000 tons per year. Because of the current high price of inositol, inositol market prospect has not been fully developed. For example, global feed production in 2013 was 960 million tons, if 0.2-0.5% of inositol was added, the amount of inositol required by feed industry should reach 190-480 million tons per year. In this case, the current domestic and even the world's production are far from meeting the demand.

At present, the traditional production method of inositol is mainly through the acid hydrolysis of phytic acid (inositol hexaphosphate) under high temperature and high pressure. This process has strict requirements for equipment, huge one-time investment, and the operating pressure can only be controlled within a certain range, limiting the utilization of raw materials; The separation process of inositol from raw product is complex, resulting in high loss of product, and relatively high production cost. Also, the process will produce a large amount of phosphate pollutants, causing serious pollution to water source and environment. In recent years, in order to reduce energy consumption and pollution, hydrolysis method under atmospheric pressure is developed. At present, the hot spots of inositol production are chemical synthesis and microbial enzymatic fermentation. However, these methods suffer the same problems of high cost and low yield of product.

Therefore, there is an urgent need to develop a new method with low-cost, low pollution and high yield for inositol production.

SUMMARY

The technical problem to be solved by the present disclosure is to provide an enzyme-catalyzed conversion method for inositol, i.e., a method for producing inositol through multi-enzyme catalyzing starch or cellulose and their derivative and glucose in vitro. The method has the advantages of high inositol yield and high conversion rate, low production cost, no pollution, and so on.

In order to solve the above-mentioned technical problems, the technical solution adopted by the present disclosure is described as follows.

The present disclosure first discloses an inositol preparation method comprising the following steps:

(1) using starch or starch derivative as substrate, adding α-glucan phosphorylase (EC 2.4.1.1), phosphoglucomutase (EC 5.4.2.2), inositol-3-phophate synthase (EC 5.5.1.4) and inositol monophosphatase (EC 3.1.3.25) to establish a multi-enzyme reaction system, and perform an enzyme-catalyzed reaction; (2) obtaining inositol from the reaction product after separation and purification.

In step (1), the concentration of the substrate is 10 g/L; the amount of the α-glucan phosphorylase is 0.05 U/mL; the amount of the phosphoglucomutase is 1 U/mL; the usage of the inositol-3-phophate synthase is 0.05 U/mL; the amount of the inositol monophosphatase is 2 U/mL. The condition for the enzyme-catalyzed reaction is: reacting at 40-80° C. for 10 to 100 hours; preferably, reacting at 60° C. for 40 hours.

Adding starch debranching enzyme and maltose phosphorylase (EC 2.4.1.8), or starch debranching enzyme and glucanotransferase (EC 2.4.1.25) to the multi-enzyme reaction system can increase the yield and conversion rate of inositol from the substrate. Preferably, the amount of the starch debranching enzyme is 1 U/mL; the amount of the maltose phosphorylase (EC 2.4.1.8) or glucanotransferase is 1 U/mL; wherein, the debranching enzyme is either one or both of isoamylase (EC 3.2.1.68) or pullulanase (EC 3.2.1.41).

More preferably, the concentration of the substrate is 10 g/L; the amount of the α-glucan phosphorylase is 5 U/mL; the amount of the phosphoglucomutase is 1 U/mL; the amount of the inositol-3-phophate synthase is 5 U/mL; the usage of the inositol monophosphatase is 2 U/mL; the usage of the starch debranching enzyme is 1 U/mL; the amount of the maltose phosphorylase or glucanotransferase is 1 U/mL.

The reaction condition of enzyme catalysis is: reacting at 40-100° C. for 10 to 100 hours; preferably, reacting at 40-80° C. for 40 hours; most preferably, reacting at 80° C. for 40 hours.

In order to further increase the yield of inositol, converting the remaining glucose into inositol, polyphosphate glucokinase (EC 2.7.1.63) and polyphosphate are added to the multi-enzyme reaction system. Preferably, the amount of the polyphosphate glucokinase is 1 U/mL; the amount of the polyphosphate is 10 mM; wherein the polyphosphate is preferably sodium polyphosphate.

The multi-enzyme reaction system further comprises the following components: buffer, inorganic phosphate, divalent magnesium ion and zinc ion or manganese ion. Preferably, the amount of each component is: 100 mM of the buffer, 10 mM of the inorganic phosphate, 5 mM of the divalent magnesium ion, 0.5 mM of the zinc ion or the manganese ion; wherein the buffer is preferably HEPES buffer; more preferably, the pH of the HEPES buffer is 7.2.

After the completion of the reaction, the residual starch residue will be pure amylose. At this point, a small amount of α-amylase (EC 3.2.1.1) can be added to promote the hydrolysis of the starch residue and further increase the production of inositol. Preferably, the amount of α-amylase is 0.1 U/ml.

In the present disclosure, starch or starch derivative is used as substrate, α-glucan phosphorylase, phosphoglucomutase, inositol-3-phophate synthase and inositol monophosphatase are added to prepare a multi-enzyme reaction system. The multi-enzyme catalyzed pathway comprises: one glucose unit at the non-reducing end of the starch or starch derivative is converted to glucose 1-phosphate by α-glucan phosphorylase; glucose 1-phosphate is converted to glucose 6-phosphate by phosphoglucomutase; glucose 6-phosphate is converted to inositol 3-phosphate by inositol 3-phophate synthase; and inositol 3-phosphate is converted to inositol by inositol monophosphatase. Because the last two reactions, converting glucose-6-phosphate to inositol-3-phosphate by inositol-3-phophate synthase and converting inositol-3-phosphate to inositol by inositol monophosphatase, are irreversible reactions, the yield of inositol from starch is high. High yield and high conversion rate can significantly reduce the cost of final inositol separation.

Starch is a mixture of amylose (20-30%) and amylopectin (70-80%). The branched chain of amylopectin is linked to the main chain via α-1,6 glycosidic bond, and α-glucan phosphorylase cannot function on α-1,6 glycosidic bond. In order to improve the yield of inositol, debranching enzyme-isoamylase or pullulanase, which is capable of decomposing the α-1,6 glycosidic bond in starch, is added to the multi-enzyme reaction system in the present disclosure. Since the final product of the hydrolyzed starch by α-glucan phosphorylase is maltose, maltose phosphorylase is added to the reaction system to utilize maltose, thus the maltose is decomposed into glucose 1-phosphate and glucose. More preferably, in the present disclosure, polyphosphate and polyphosphate glucokinase are further added to the multi-enzyme reaction system to convert the glucose to glucose 6-phosphate, which is converted to inositol by inositol 3-phosphate synthase and inositol monophosphatase. Finally, all the glucose units in starch and its derivative are converted to inositol, resulting in high inositol production yield. Herein, maltose phosphorylase can be replaced by 4-α-glucanotransferase (EC. 2.4.1.25), which can polymerize short chain oligosaccharides into long chain oligosaccharides, and the long chain oligosaccharides can be reused by α-glucan phosphorylase, thus improving the utilization of starch.

The starch in the present disclosure is preferably a soluble starch; the starch derivative comprises any one or more of partially hydrolyzed starch, starch dextrin, maltodextrin, malto oligosaccharide or maltose.

The present disclosure also describes another inositol preparation method comprising the following steps:

(1) using cellulose or cellulose derivative as the substrate, adding cellulase, cellodextrin phosphorylase (EC 2.4.1.49), cellobiose phosphorylase (EC 2.4.1.20), phosphoglucomutase (EC 5.4.2.2), inositol 3-phophate synthase (EC 5.5.1.4) and inositol monophosphatase (EC 3.1.3.25) to establish a multi-enzyme reaction system to perform an enzyme-catalyzed reaction; (2) obtaining inositol from reaction raw product after separation and purification.

In the present disclosure, cellulose is used as a substrate. Cellulase, cellodextrin phosphorylase, cellobiose phosphorylase, phosphoglucomutase, inositol 3-phophate synthase and inositol monophosphatase are added to prepare a multi-enzyme reaction system. The multi-enzyme catalyzed pathway comprises: cellulose is hydrolyzed by cellulase to produce cellodextrin and cellobiose; one glucose unit in the cellodextrin or cellobiose is converted to glucose 1-phosphate by cellodextrin phosphorylase and cellobiose phosphorylase; glucose 1-phosphate is converted to glucose 6-phosphate by phosphoglucomutase; glucose 6-phosphate is converted to inositol 3-phosphate by inositol 3-phophate synthase; and inositol 3-phosphate is converted to inositol by inositol monophosphatase.

Preferably, the reaction condition of step (1) is: 10 g/L cellulose or cellulose derivative and 5 U/ml cellulase are mixed in an ice-water bath and stood in the ice-water bath for 5 minutes; the mixture is centrifuged at 4° C. and supernatant is discarded to give a mixture of cellulase and cellulose. This treatment can remove almost all glucosidase from commercial cellulase, which avoids the generation of large amount of glucose from hydrolyzing cellobiose by glucosidase, so that the major hydrolysates are cellobiose and cellodextrin.

In the multi-enzyme reaction system, the concentration of the mixture of cellulase and cellulose is 10 g/L; the amount of the cellodextrin phosphorylase is 5 U/mL; the amount of the cellobiose phosphorylase is 5 U/mL; the amount of the phosphoglucomutase is 1 U/mL; the amount of the inositol 3-phophate synthase is 5 U/mL; and the amount of the inositol monophosphatase is 2 U/mL. The condition for the enzyme-catalyzed reaction is: reacting at 20-100° C. for 10 to 100 hours; preferably, reacting at 40-80° C. for 72 hours; most preferably, reacting at 50° C. for 72 hours.

In order to further increase the product yield of inositol, polyphosphate glucokinase (EC 2.7.1.63) and polyphosphate are added to the multi-enzyme reaction system of step (1). Preferably, the amount of the polyphosphate glucokinase is 5 U/mL; the amount of the polyphosphate is 10 mM; wherein the polyphosphate is preferably sodium polyphosphate.

In order to improve the efficiency of the enzyme-catalyzed reaction and the product yield, in addition to all the enzymes, the multi-enzyme reaction system further comprises the following components: buffer, inorganic phosphate, divalent magnesium ion and zinc ion or manganese ion. Preferably, the amount of each component is: 100 mM of the buffer, 10 mM of the inorganic phosphate, 5 mM of the divalent magnesium ion, 0.5 mM of the zinc ion or the manganese ion; wherein the buffer is preferably HEPES buffer, more preferably, the pH of the HEPES buffer is 7.2.

Polyphosphate glucokinase and polyphosphate are further added to the multi-enzyme reaction system of the present disclosure, converting glucose, which is the final product of cellulose hydrolysis, to glucose-6-phosphate; then glucose-6-phosphate is converted to inositol by inositol 3-phophate synthase and inositol monophosphatase. Eventually, all the glucose units in cellulose and its derivative are converted to inositol.

The cellulose derivative of the present disclosure includes any one of product after cellulose-pretreatment, cellodextrin or cellobiose;

wherein, there are many kinds of cellulose pretreatment methods, such as acid hydrolysis, enzyme hydrolysis, physical method and so on; the product after the cellulose pretreatment in the present disclosure is preferably a product via cellulose treatment with concentrated phosphoric acid.

Any one of the enzymes in the multi-enzyme reaction system of the present disclosure may also be replaced by any enzyme having the same function, preferably a mutant enzyme generated by protein engineering having the same function.

In a test, the present disclosure which converts starch to inositol by multi-enzyme catalysis in vitro in one pot, when soluble starch was used as raw material, and α-glucan phosphorylase, phosphoglucomutase, inositol 3-phosphate synthase and inositol monophosphatase were added to catalyze the reaction, the final inositol yield was 16%. After adding isoamylase, maltose phosphorylase, polyphosphate glucokinase and sodium polyphosphate to the above reaction system at the meantime, increasing the amount of glucan phosphorylase and inositol 3-phophate synthase, made the final inositol yield reach 72%, improving the yield significantly.

In an embodiment of the present disclosure, which converts cellulose to inositol by multi-enzyme catalysis in vitro in one pot, microcrystalline cellulose (Avicel) was used as substrate, and cellulose, cellodextrin phosphorylase, cellobiose phosphorylase, phosphoglucomutase, inositol 3-phosphate synthase and inositol monophosphatase were added to catalyze the reaction, the final inositol yield was 14%; when regenerated amorphous cellulose was used as substrate, and cellulose, cellodextrin phosphorylase, cellobiose phosphorylase, phosphoglucomutase, inositol 3-phosphate synthase and inositol monophosphatase were added to catalyze the reaction, the final inositol yield was 48%. Further adding polyphosphate glucokinase and sodium polyphosphate, made the final inositol yield reach 65%, improving the yield significantly.

The technical solution of the present disclosure has the following beneficial effects compared with the prior art:

In a multi-enzyme reaction system of the present disclosure, starch or cellulose and their derivatives are used as raw materials and converted to inositol through multi-enzyme catalyzed reaction in vitro; through process optimization, by adding enzyme to promote the hydrolysis of starch or cellulose and enzyme to use the by-product (glucose), the conversion efficiency is significantly improved. High yield reduces the cost of inositol separation greatly, resulting in the low product cost of inositol. The method of the present disclosure has advantages such as simple process, high raw material utilization yield, high product yield, low product cost and low pollution, and easy scale up of inositol production.

Terms and Definitions Used in the Present Disclosure

Unless otherwise defined, all technical and scientific terms used herein have the same meaning as commonly understood by one of ordinary skill in the art to which this invention belongs.

The term "enzyme-catalyzed reaction" refers to a chemical reaction carried out under the action of biocatalyst-enzyme.

The term "glucose polymer" refers to starch or cellulose, which are polymer of glucose molecule.

The term "glucose oligomer" refers to partially hydrolyzed starch, starch dextrin, malto oligosaccharide, maltose, cellodextrin or cellobiose, and so on.

BRIEF DESCRIPTION OF DRAWINGS

FIG. 2 shows the detection of four key enzymes by SDS-PAGE. Wherein: lane 1, α-glucan phosphorylase; lane 2, phosphoglucomutase; lane 3, inositol 3-phophate synthase; lane 4, inositol monophosphatase.

FIG. 3a shows the identification of inositol, glucose, glucose-1-phosphate and glucose-6-phosphate by HPLC; FIG. 3b shows the inositol concentration by HPLC quantitative analysis, which is calculated from the height of inositol peak.

DETAILED DESCRIPTION

The present disclosure is further described in connection with specific examples and the advantages and features of the present disclosure will be more apparent from the description. It is to be understood that the examples are exemplary only and are not intended to limit the scope of the present disclosure. It will be understood by those of ordinary skill in the art that the details and form of the invention may be modified or replaced without departing from the spirit and scope of the present disclosure, but such modifications or replacements fall within the scope of the present disclosure.

Experimental Materials

Soluble starch, ACROS, Cat No. 424490020

Maltodextrin, ALDRICH, Cat No. 419672 pET20b vector, Novagen (Madison, Wis., USA)

*Escherichia coli* expressing bacteria BL21 (DE3), Invitrogen (Carlsbad, Calif., USA)

Most of the enzymes in the present disclosure (except inositol monophosphatase, polyphosphate glucokinase and glucanotransferase) are commercially available from Sigma. They can all be obtained by prokaryotic expression through genetic engineering methods.

Cellulase, purchased from Sigma, Cat No. C2730

Maltose phosphorylase, purchased from Sigma, Cat No. M8284

α-amylase, purchased from Sigma, Cat No. 10065

Avicel, microcrystalline cellulose, purchased from Sigma, Cat No. 11365

EXAMPLES

Figure 1:
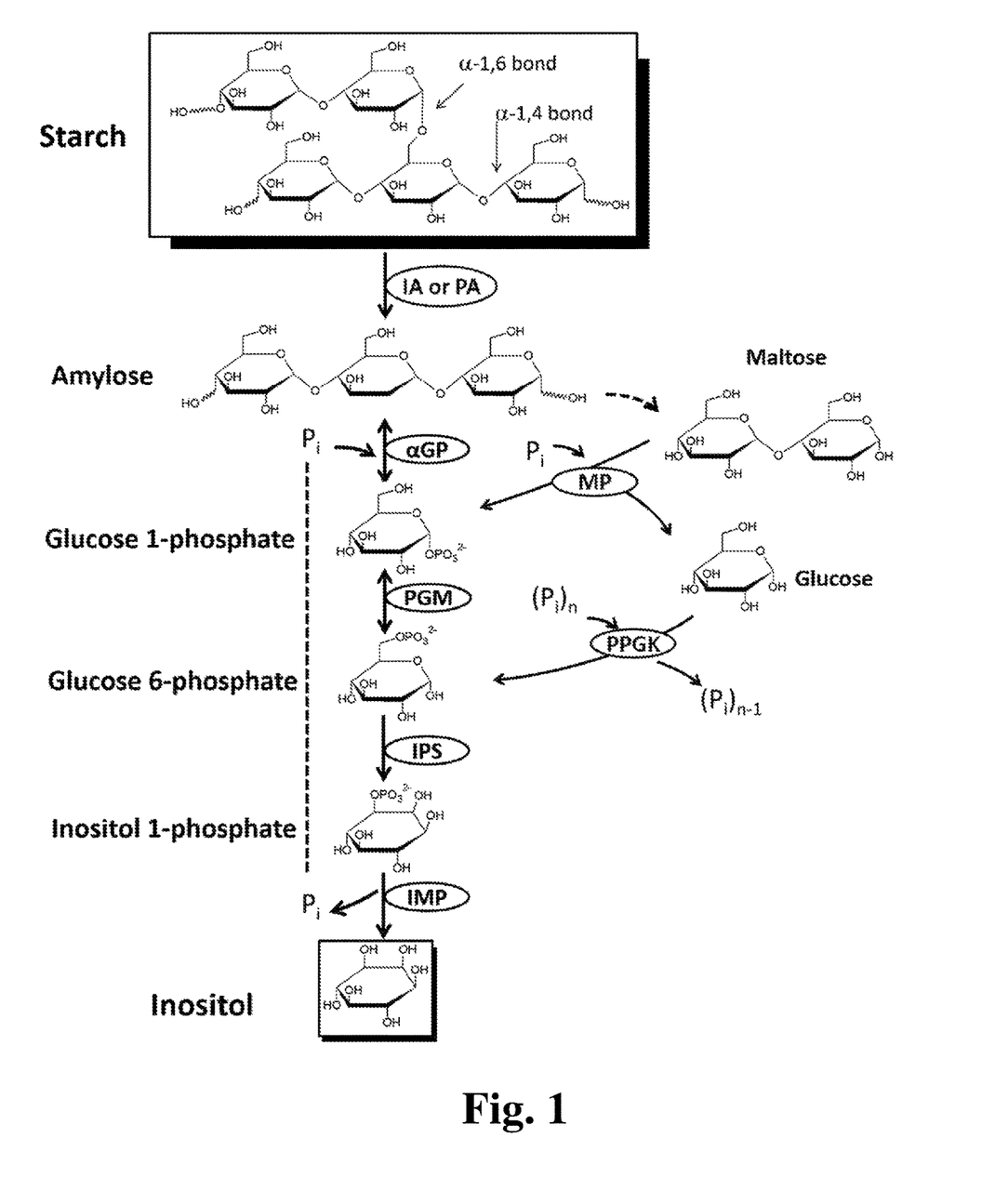
FIG. 1 is a schematic showing the multi-enzymatic catalytic pathway of converting starch to inositol in vitro. Wherein: IA, isoamylase; PA, pullulanase; αGP, α-glucan phosphorylase; PGM, phosphoglucomutase; IPS, inositol 3-phophate synthase; IMP, inositol monophosphatase; MP, maltose phosphorylase (which can be replaced by glucanotransferase); PPGK, polyphosphate glucokinase.

Example 1. Conversion of Starch to Inositol Through In Vitro Multi-Enzyme Catalysis Starch is converted to inositol through an in vitro multi-enzyme catalyzed system (FIG. 1). The key enzymes include: (1) α-glucan phosphorylase (αGP, EC 2.4.1.1), releasing glucose 1-phosphate from starch; (2) phosphoglucomutase (PGM, EC 5.4.2.2), catalyzing glucose 1-phosphate to glucose-6-phosphate; (3) inositol 3-phophate synthase (IPS, EC 5.5.1.4), catalyzing glucose 6-phosphate to inositol 3-phosphate; (4) inositol monophosphatase (IMP, EC 3.1.3.25), catalyzing the dephosphorylation of inositol 3-phosphate to inositol. Since the last two enzymatic reactions are irreversible, the enzyme-catalyzed system has a very high yield.

Figure 2:
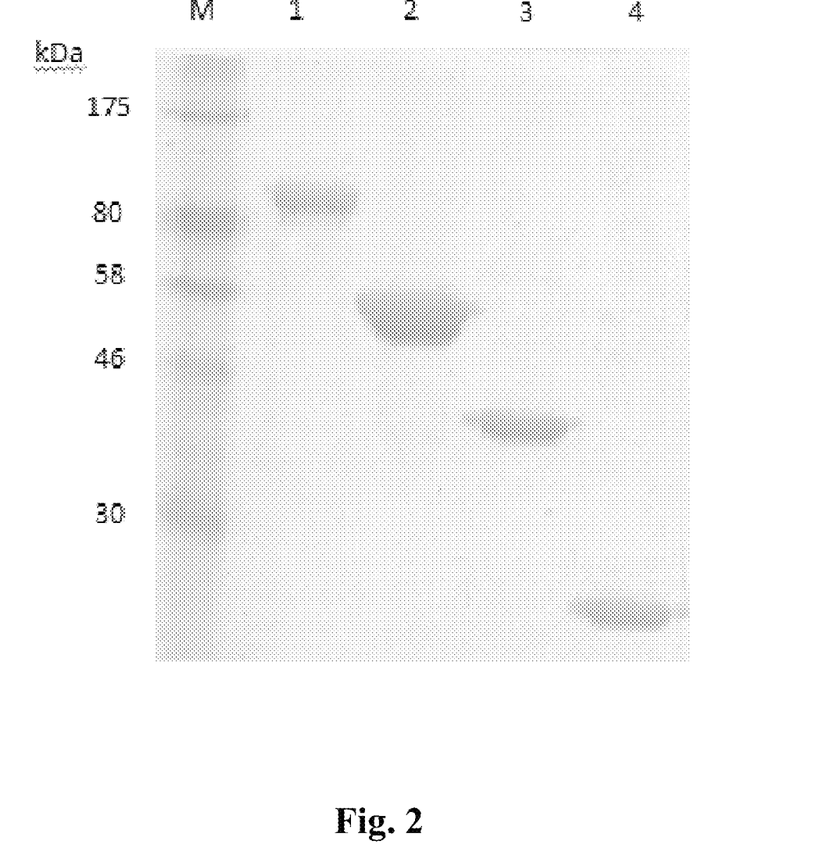

In the present disclosure, α-glucan phosphorylase was from *Thermotoga maritime* and the gene number on KEGG is TM1168; phosphoglucomutase was also from *T. maritime* and the gene number on KEGG was TM0769; inositol 3-phophate synthase is from *Archaeoglobus fulgidus* and the gene number on KEGG is AF1794; inositol monophosphatase is also from *T. maritime* and the gene number on KEGG is TM1415. All these genomic DNAs are available from ATCC official website (www.atcc.org). The four genes were obtained from the corresponding genomic DNA by PCR using different primers and cloned into the pET20b vector (Novagen, Madison, Wis.) by Simple Cloning (You, C., et al. (2012), "Simple Cloning via Direct Transformation of PCR Product (DNA Multimer) to *Escherichia coli* and *Bacillus subtilis*." Appl. Environ. Microbiol. 78(5): 1593-1595.), to obtain corresponding expression vectors: pET20b-TmαGP, pET20b-AfIPS, pET20b-TmPGM and pET20b-TmIMP. These four plasmids were transformed into *E. coli* BL21 (DE3) (Invitrogen, Carlsbad, Calif.), and protein expression and purification were carried out. The results of protein purification were shown in FIG. 2.

A 0.75 ml reaction system comprising 100 mM HEPES buffer (pH 7.2), 10 mM inorganic phosphate, 5 mM divalent magnesium ion, 0.5 mM zinc ion, 0.05 U/mL α-glucan phosphorylase, 1 U/mL phosphoglucomutase, 0.05 U/mL inositol-3-phosphate synthase, 2 U/mL inositol monophosphate and 10 g/L of soluble starch, was subjected to catalytic reaction at 60° C. for 40 hours.

Figure 3A:
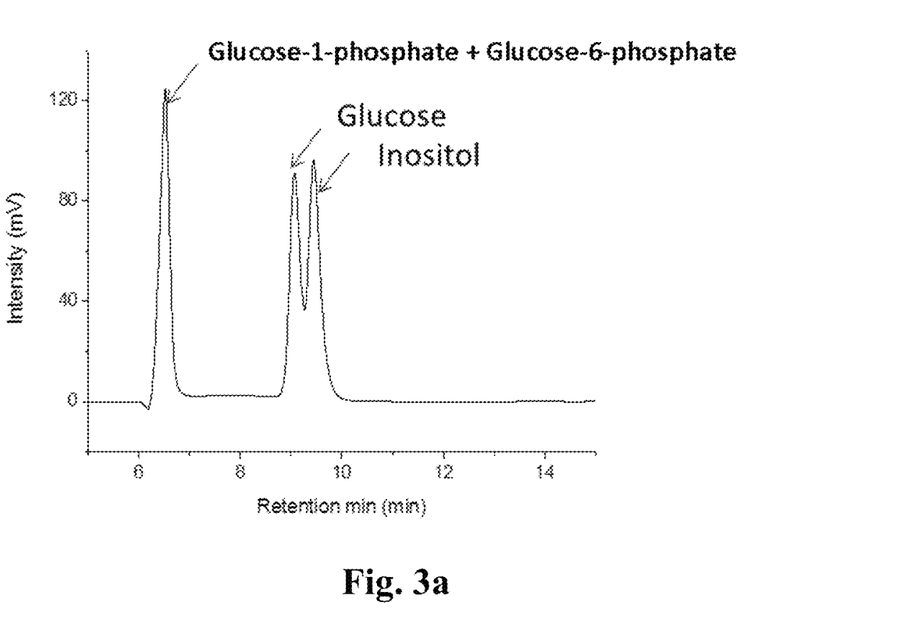
FIGS. 3a and 3b show analysis of inositol by HPLC.
Figure 3B:
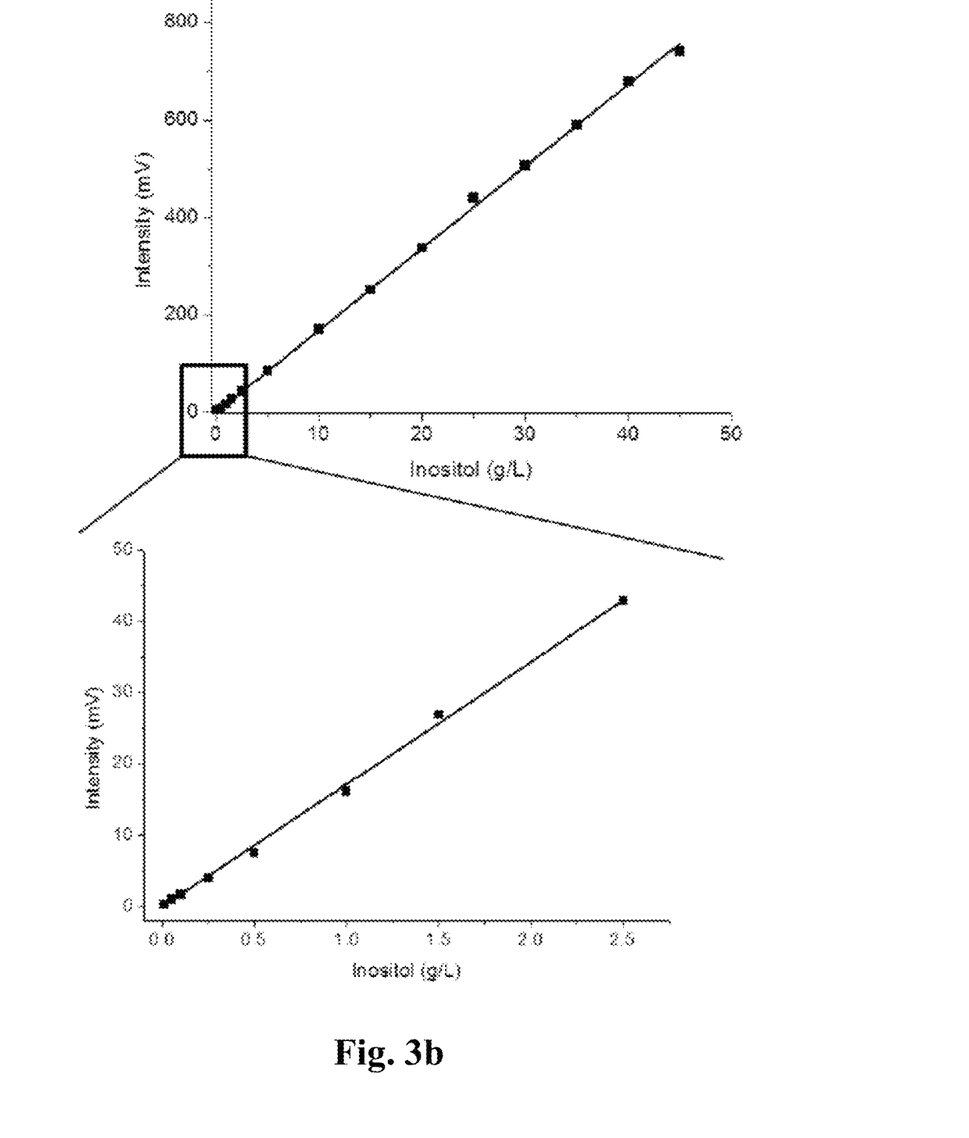

Depending on the retention time, HPLC can be used to distinguish inositol, glucose, glucose 1-phosphate or glucose 6-phosphate in the reaction solution (FIG. 3a); the inositol can be quantified by HPLC, as shown in FIG. 3b, the concentration of inositol is proportional to the height of the inositol characteristic peak in HPLC. The mobile phase of HPLC was 5 mM dilute sulfuric acid.

Figure 4:
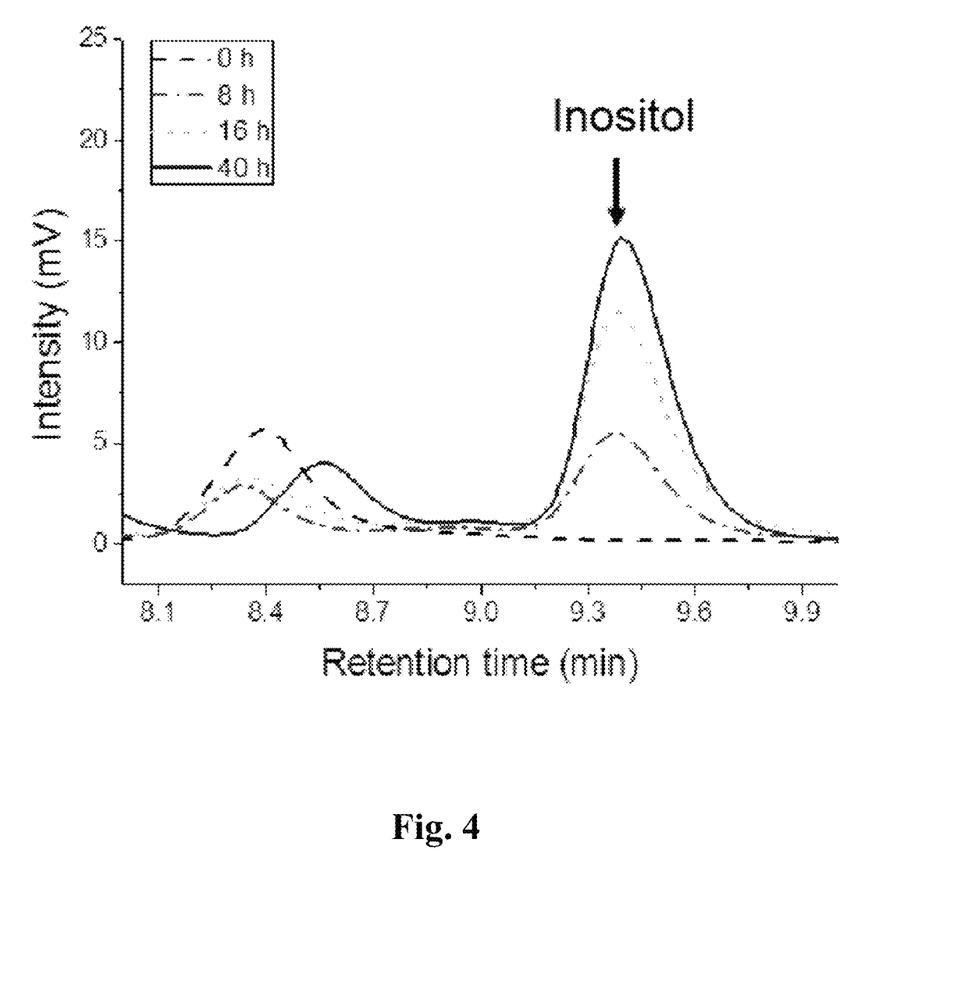
FIG. 4 shows the product detected by HPLC after enzyme-catalyzed reaction in which soluble starch is used as substrate. The arrow indicates the characteristic peak of inositol.

After the completion of reaction, the final concentration of the final inositol (FIG. 4) was 1.6 g/L and the yield was 16%.

Example 2. Conversion of Starch to Inositol Through In Vitro Multi-Enzyme Catalysis The preparations of α-glucan phosphorylase, phosphoglucomutase, inositol 3-phophate synthase and inositol monophosphatase are the same as in Example 1.

A 0.75 ml reaction system comprising 100 mM HEPES buffer (pH 7.2), 10 mM inorganic phosphate, 5 mM divalent magnesium ion, 0.5 mM zinc ion, 0.05 U/mL α-glucan phosphorylase, 1 U/mL phosphoglucomutase, 0.05 U/mL inositol-3-phosphate synthase, 2 U/mL inositol monophosphate and 10 g/L of soluble starch, was subjected to catalytic reaction at 40° C. for 40 hours.

After the completion of reaction, the final concentration of the final inositol was 0.9 g/L and the yield was 9%.

Example 3. Conversion of Starch to Inositol Through In Vitro Multi-Enzyme Catalysis The preparations of α-glucan phosphorylase, phosphoglucomutase, inositol 3-phophate synthase and inositol monophosphatase are the same as in Example 1.

A 0.75 ml reaction system comprising 100 mM HEPES buffer (pH 7.2), 10 mM inorganic phosphate, 5 mM divalent magnesium ion, 0.5 mM zinc ion, 0.05 U/mL α-glucan phosphorylase, 1 U/mL phosphoglucomutase, 0.05 U/mL inositol-3-phosphate synthase, 2 U/mL inositol monophosphate and 10 g/L of soluble starch, was subjected to catalytic reaction at 80° C. for 40 hours.

After the completion of reaction, the final concentration of the final inositol was 3.6 g/L and the yield was 36%.

Example 4. Conversion of Starch to Inositol by In Vitro Multi-Enzyme Catalysis Through Process Optimization and Addition of Enzyme that Promotes Starch Hydrolysis The use of glucan phosphorylase alone cannot completely hydrolyze starch, since starch has branch chain which is linked to main chain with α-1,6 glycosidic bond, and α-glucan phosphorylase only acts on α-1,4 glycosidic bond. This requires the addition of isoamylase (EC 3.2.1.68) to hydrolyze the α-1,6 glycosidic bond. Finally, the final products of starch hydrolysis by these two enzymes are maltose and glucose. In order to convert the final products to inositol, further adding of maltose phosphorylase (EC 2.4.1.8) and polyphosphate glucokinase (EC 2.7.1.63) is needed.

In the present disclosure, isoamylase is from *Sulfolobus tokodaii* and the gene number on KEGG is ST0928; the genomic DNA of this strain is kindly provided by Professor Georg Fuchs in Albert-Ludwigs-Universität Freiburg (Germany). Polyphosphate glucokinase is from *Thermobifida fusca* and the gene number on KEGG is Tfu1811; the genomic DNA of this strain is kindly provided by Professor David Wilson in Cornell University (USA). Glucanotransferase is from *Thermococcus litoralis* and the gene number on KEGG is OCC_10078; the genomic DNA of this strain is available from ATCC official website (www.atcc.org). These three genes are obtained from the corresponding genomic DNAs by PCR using different primers and cloned into the pET20b vector by Simple Cloning (You, C., et al. (2012), "Simple Cloning via Direct Transformation of PCR Product (DNA Multimer) to *Escherichia coli* and *Bacillus subtilis*." Appl. Environ. Microbiol. 78(5): 1593-1595.), to obtain corresponding expression vectors: pET20b-StIA, pET20b-TfuPPGK and pET20b-T14GT. These three plasmids were transformed into *E. coli* BL21 (DE3) (Invitrogen, Carlsbad, Calif.), and protein expression and purification were carried out.

The preparation of α-glucan phosphorylase, phosphoglucomutase, inositol 3-phophate synthase and inositol monophosphatase are the same as in Example 1. Maltose phosphorylase was purchased from Sigma, Cat No. M8284.

A 0.75 ml reaction system comprising 100 mM HEPES buffer (pH 7.2), 10 mM inorganic phosphate, 5 mM divalent magnesium ion, 0.5 mM zinc ion, 5 U/mL α-glucan phosphorylase, 1 U/mL phosphoglucomutase, 5 U/mL inositol-3-phosphate synthase, 2 U/mL inositol monophosphate, 1 U/mL isoamylase, 1 U/mL maltose phosphorylase, 1 U/mL polyphosphate glucokinase, 10 mM sodium polyphosphate and 10 g/L of soluble starch, was subjected to catalytic reaction at 80° C. for 40 hours. The final concentration of the final inositol (FIG. 4) was 7.2 g/L and the yield reached 72%.

Example 5. Conversion of Starch to Inositol by In Vitro Multi-Enzyme Catalysis Through Process Optimization and Addition of Enzyme that Promotes Starch Hydrolysis The preparation of α-glucan phosphorylase, phosphoglucomutase, inositol 3-phophate synthase and inositol monophosphatase are the same as in Example 1. The preparation of polyphosphate glucokinase is the same as in Example 4. Pullulanase (EC 3.2.1.41) was purchased from Sigma, Cat No. P1067; maltose phosphorylase was purchased from Sigma, Cat No. M8284.

Since the pullulanase purchased from sigma does not react at high temperatures (80° C.), soluble starch was treated with pullulanase at 37° C. first, followed by adding other enzymes. The reaction was carried out at 80° C.

A 0.75 ml reaction system comprising 100 mM HEPES buffer (pH 7.2), 10 mM inorganic phosphate, 5 mM divalent magnesium ion, 0.5 mM zinc ion, 1 U/mL pullulanase, 10 mM sodium polyphosphate and 10 g/L of soluble starch, was subjected to catalytic reaction at 37° C. After 10 hours, 5 U/mL α-glucan phosphorylase, 1 U/mL phosphoglucomutase, 5 U/mL inositol 3-phosphate synthase, 2 U/mL inositol monophosphate, 1 U/mL maltose phosphorylase and 1 U/mL polyphosphate glucokinase were added and the catalytic reaction was carried out at 80° C. for 40 hours. The final concentration of the final inositol (FIG. 4) was 7.3 g/L and the yield reached 73%.

Subsequently, a small amount of α-amylase was added to the reaction system to promote the hydrolysis of the residual starch and increase the production of inositol. The amount of α-amylase was 0.1 U/ml and the reaction was performed at 37° C. for 6 hours then at 80° C. for 24 hours. The final concentration of the final inositol was 8.8 g/L and the yield reached 88%.

Example 6. Conversion of Maltodextrin to Inositol Through In Vitro Multi-Enzyme Catalysis The preparation of α-glucan phosphorylase, phosphoglucomutase, inositol 3-phophate synthase and inositol monophosphatase are the same as in Example 1. The preparation of isoamylase and polyphosphate glucokinase are the same as in Example 4. Maltose phosphorylase was purchased from Sigma, Cat No. M8284.

Figure 5:
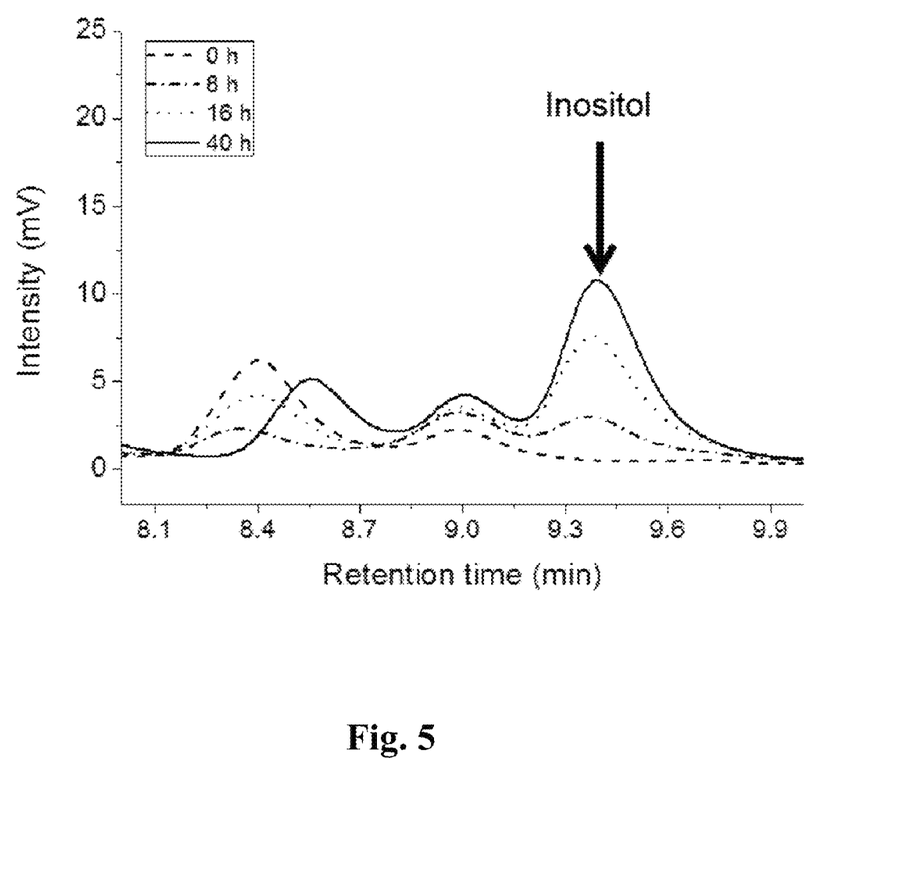
FIG. 5 shows the product detected by HPLC after enzyme-catalyzed reaction in which maltodextrin is used as substrate. The arrow indicates the characteristic peak of the inositol.

A 0.75 ml reaction system comprising 100 mM HEPES buffer (pH 7.2), 10 mM inorganic phosphate, 5 mM divalent magnesium ion, 0.5 mM zinc ion, 5 U/mL α-glucan phosphorylase, 1 U/mL phosphoglucomutase, 5 U/mL inositol 3-phosphate synthase, 2 U/mL inositol monophosphate, 1 U/mL isoamylase, 1 U/mL maltose phosphorylase, 1 U/mL polyphosphate glucokinase, 10 mM sodium polyphosphate and 10 g/L of maltodextrin (ALDRICH, Cat No. 419672), was subjected to catalytic reaction at 80° C. for 40 hours. The final concentration of the final inositol (FIG. 5) was 7.8 g/L and the yield reached 78%.

Figure 6:
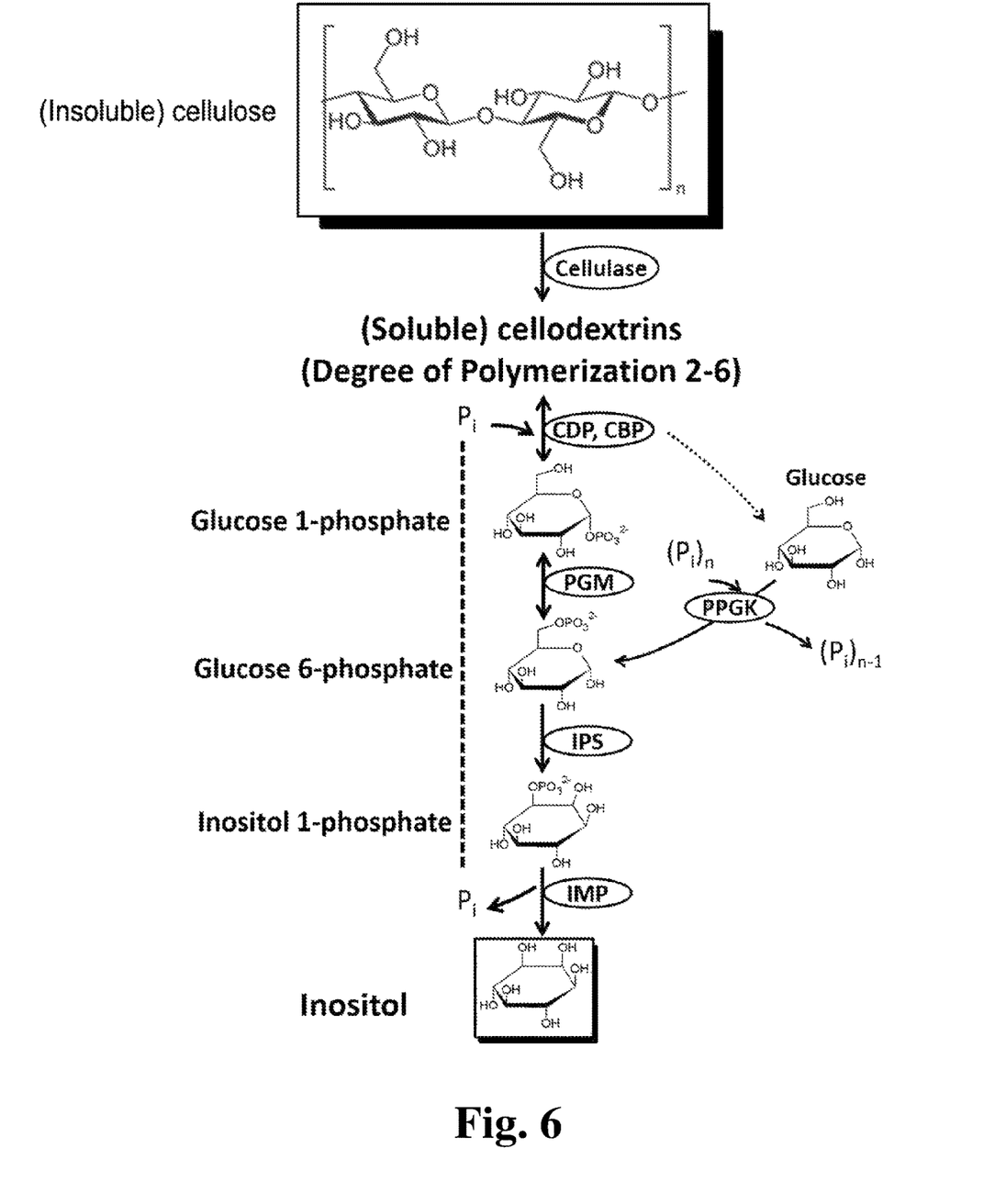
FIG. 6 is a schematic showing the multi-enzymatic catalytic pathway of converting cellulose to inositol in vitro. Wherein: cellulase, cellulase; CDP, cellodextrin phosphorylase; CBP, cellobiose phosphorylase; PGM, phosphoglucomutase; IPS, inositol 3-phosphate synthase; IMP, inositol monophosphatase; PPGK, polyphosphate glucokinase.

Example 7. Conversion of Cellulose to Inositol Through In Vitro Multi-Enzyme Catalysis Schematic of conversion of cellulose to inositol through multi-Enzyme catalysis in vitro is shown in FIG. 6.

Cellulase is from Sigma, Cat No. C2730; the preparation of phosphoglucomutase, inositol-3-phophate synthase and inositol monophosphatase are the same as in Example 1.

Figure 7:
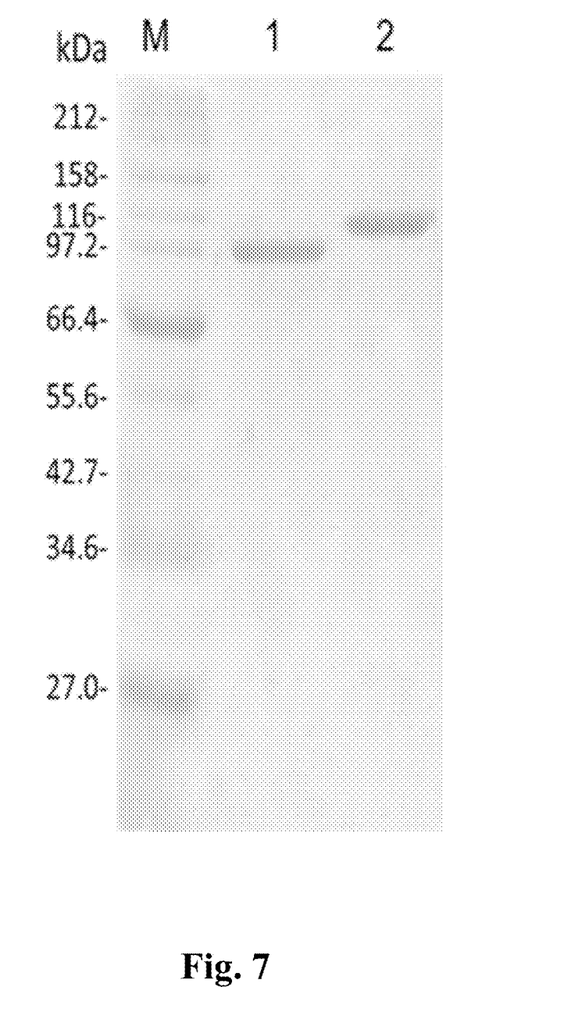
FIG. 7 shows the detection of two key enzymes in the conversion of cellulose to inositol by SDS-PAGE. Wherein: lane 1, cellobiose phosphorylase; lane 2, cellodextrin phosphorylase.

Cellodextrin phosphorylase (Cthe_2989) and cellobiose phosphorylase (Cthe_0275) are both from *Clostridium thermocellum*. These two genes are obtained from the corresponding genomic DNAs (genomic DNA is available from ATCC official website (www.atcc.org)) by PCR using different primers and cloned into the pET20b vector by Simple Cloning (You, C., et al. (2012)) to obtain corresponding expression vectors: pET20b-CthCDP and pET20b-CthCBP. The two plasmids were both transformed into *E. coli* BL21 (DE3) and protein expression and purification were carried out. The results of protein purification were shown in FIG. 7.

In this experiment, microcrystalline cellulose (Avicel) was used as substrate. First, commercial cellulase (5 U/ml) and cellulose (10 g/L) were mixed in an ice-water bath and stood for 5 minutes; the mixture was centrifuged at 4° C. and supernatant was discarded. The pellet was a mixture of cellulose and cellulase which can bind to cellulose. This treatment can remove almost all glucosidase from commercial cellulase, avoiding the generation of large amount of glucose from hydrolyzation of cellobiose by glucosidase, so that the major hydrolysates are cellobiose and cellodextrin.

Figure 8:
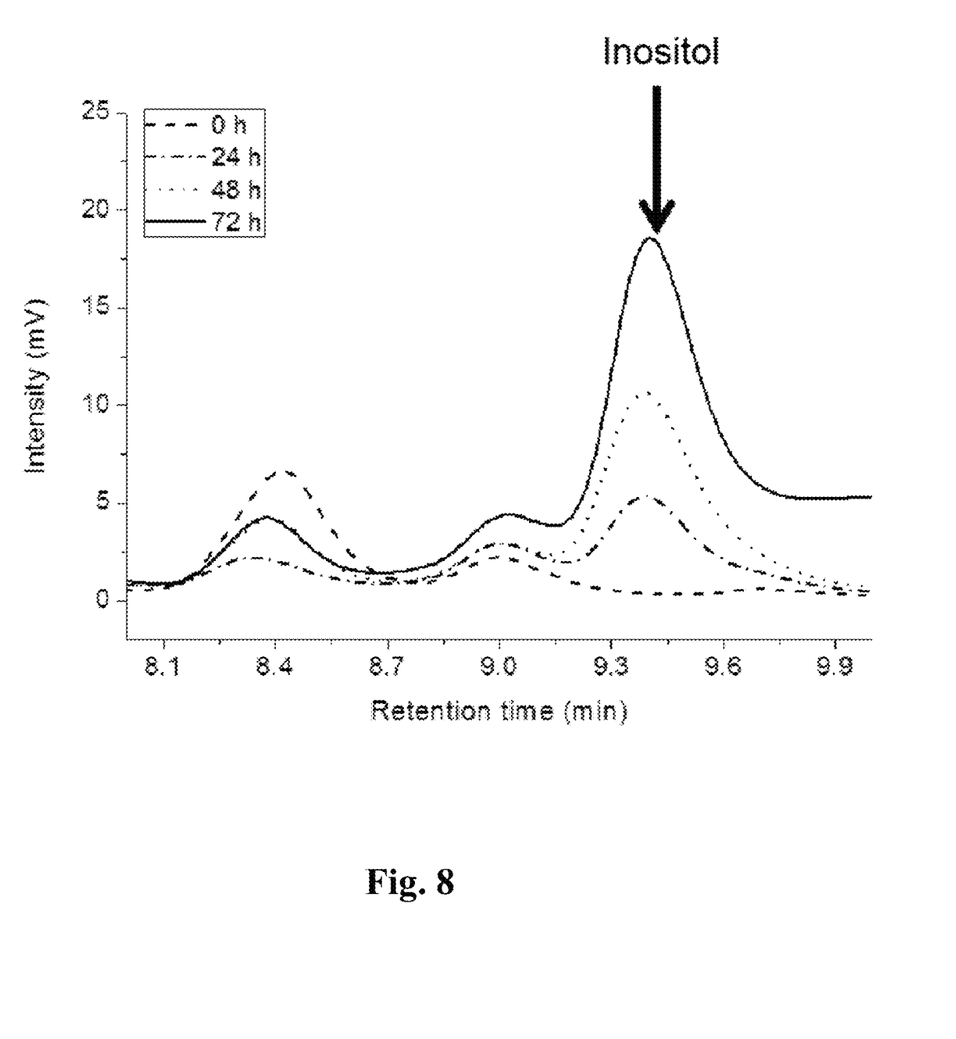
FIG. 8 shows the product detected by HPLC after enzyme-catalyzed reaction in which microcrystalline cellulose (Avicel) is used as substrate. The arrow indicates the characteristic peak of the inositol.

A 0.75 ml reaction system comprising 100 mM HEPES buffer (pH 7.2), 10 mM inorganic phosphate, 5 mM divalent magnesium ion, 0.5 mM zinc ion, 5 U/mL cellodextrin phosphorylase, 5 U/mL cellobiose phosphorylase, 1 U/mL phosphoglucomutase, 5 U/mL inositol 3-phosphate synthase, 2 U/mL inositol monophosphate and 10 g/L of the mixture of cellulose and cellulase, was subjected to catalytic reaction at 50° C. for 72 hours. The final concentration of the final inositol was 1.4 g/L and the yield reached 14%, as shown in FIG. 8.

Example 8. Conversion of Cellulose to Inositol Through In Vitro Multi-Enzyme Catalysis Cellulase is from Sigma, Cat No. C2730; the preparation of phosphoglucomutase, inositol 3-phophate synthase and inositol monophosphatase are the same as in Example 1; the preparation of cellodextrin phosphorylase and cellobiose phosphorylase are the same as in Example 7.

In this experiment, regenerated amorphous cellulose (RAC) was used as substrate, which is the product of Avicel after concentrated phosphoric acid treatment (Zhang, Y. H. P., et al. (2006), "A Transition from Cellulose Swelling to Cellulose Dissolution by o-Phosphoric Acid: Evidence from Enzymatic Hydrolysis and Supramolecular Structure." Biomacromolecules 7(2): 644-648.). First, commercial cellulase (5 U/ml) and cellulose (10 g/L) were mixed in an ice-water bath and stood in the ice-water bath for 5 minutes; the mixture was centrifuged at 4° C. and supernatant was discarded. The pellet was a mixture of cellulose and cellulase which can bind to cellulose.

A 0.75 ml reaction system comprising 100 mM HEPES buffer (pH 7.2), 10 mM inorganic phosphate, 5 mM divalent magnesium ion, 0.5 mM zinc ion, 5 U/mL cellodextrin phosphorylase, 5 U/mL cellobiose phosphorylase, 1 U/mL phosphoglucomutase, 5 U/mL inositol-3-phosphate synthase, 2 U/mL inositol monophosphate and 10 g/L of the mixture of cellulose and cellulase, was subjected to catalytic reaction at 50° C. for 72 hours. The final concentration of the final inositol was 4.8 g/L and the yield reached 48%.

Example 9. Conversion of Cellulose to Inositol Through In Vitro Multi-Enzyme Catalysis Cellulase is from Sigma, Cat No. C2730. The preparation of phosphoglucomutase, inositol-3-phophate synthase and inositol monophosphatase are the same as in Example 1; the preparations of cellodextrin phosphorylase and cellobiose phosphorylase are the same as in Example 7.

A 0.75 ml reaction system comprising 100 mM HEPES buffer (pH 7.2), 10 mM inorganic phosphate, 5 mM divalent magnesium ion, 0.5 mM zinc ion, 5 U/mL cellodextrin phosphorylase, 5 U/mL cellobiose phosphorylase, 1 U/mL phosphoglucomutase, 5 U/mL inositol 3-phosphate synthase, 2 U/mL inositol monophosphate and 10 g/L of the mixture of cellulose and cellulose in Example 8, was subjected to catalytic reaction at 40° C. for 72 hours. The final concentration of the final inositol was 2.3 g/L and the yield reached 23%.

Example 10. Conversion of Cellulose to Inositol Through In Vitro Multi-Enzyme Catalysis Cellulase is from Sigma, Cat No. C2730; the preparation of phosphoglucomutase, inositol 3-phophate synthase and inositol monophosphatase are the same as in Example 1; the preparation of cellodextrin phosphorylase and cellobiose phosphorylase are the same as in Example 7.

A 0.75 ml reaction system comprising 100 mM HEPES buffer (pH 7.2), 10 mM inorganic phosphate, 5 mM divalent magnesium ion, 0.5 mM zinc ion, 5 U/mL cellodextrin phosphorylase, 5 U/mL cellobiose phosphorylase, 1 U/mL phosphoglucomutase, 5 U/mL inositol 3-phosphate synthase, 2 U/mL inositol monophosphate and 10 g/L of the mixture of cellulose and cellulose in Example 8, was subjected to catalytic reaction at 80° C. for 72 hours. The final concentration of the final inositol was 1.9 g/L and the yield reached 19%.

Example 11. Conversion of Cellulose to Inositol Through Multi-Enzyme Catalysis In Vitro Since the final product after cellulose hydrolysis is glucose, it is necessary to add polyphosphate glucokinase and polyphosphoric acid to convert it to inositol.

Cellulase is from Sigma, Cat No. C2730; the preparation of phosphoglucomutase, inositol 3-phophate synthase and inositol monophosphatase are the same as in Example 1; the preparation of polyphosphate glucokinase is the same as in Example 4; and the preparation of cellodextrin phosphorylase and cellobiose phosphorylase are the same as in Example 7.

A 0.75 ml reaction system comprising 100 mM HEPES buffer (pH 7.2), 10 mM inorganic phosphate, 5 mM divalent magnesium ion, 0.5 mM zinc ion, 5 U/mL cellodextrin phosphorylase, 5 U/mL cellobiose phosphorylase, 1 U/mL phosphoglucomutase, 5 U/mL inositol 3-phosphate synthase, 2 U/mL inositol monophosphate, 10 g/L of the mixture of cellulose and cellulose in Example 8, 5 U/mL polyphosphate glucokinase and 10 mM sodium polyphosphate, was subjected to catalytic reaction at 50° C. for 72 hours. The final concentration of the final inositol (FIG. 8) was 6.5 g/L and the yield reached 65%.

The invention claimed is:

1. A method for preparing inositol, comprising:
(1) using starch or starch derivative as substrate, adding α-glucan phosphorylase, phosphoglucomutase, inositol-3-phosphate synthase and inositol monophosphatase to establish an in vitro multi-enzyme reaction system and perform an enzyme-catalyzed reaction; and
(2) separating and purifying reaction product to obtain inositol,
wherein the starch derivative of step (1) is selected from the group consisting of partially hydrolyzed starch, starch dextrin, maltodextrin, malto-oligosaccharide, and maltose,
wherein the enzyme-catalyzed reaction is performed at 60-80° C.,
wherein the multi-enzyme reaction system further comprises starch debranching enzyme, α-amylase, and one or both of maltose phosphorylase and glucanotransferase,
wherein the starch debranching enzyme is one or both of isoamylase and pullulanase,
wherein the multi-enzyme reaction system further comprises polyphosphate glucokinase and polyphosphate;
wherein the polyphosphate is sodium polyphosphate.

2. The preparation method according to claim 1, wherein the multi-enzyme reaction system further comprises the following components: buffer, inorganic phosphate anion, divalent magnesium ion, and either zinc ion or manganese ion.

* * * * *